(12) United States Patent
Kahmer et al.

(10) Patent No.: US 10,925,740 B2
(45) Date of Patent: Feb. 23, 2021

(54) INTERVERTEBRAL SPACER WITH CHAMFERED EDGES

(71) Applicant: GLOBUS MEDICAL, INC., Audubon, PA (US)

(72) Inventors: Damien Kahmer, Philadelphia, PA (US); Mark Weiman, Downingtown, PA (US)

(73) Assignee: Globus Medical Inc., Audubon, PA (US)

( * ) Notice: Subject to any disclaimer, the term of this patent is extended or adjusted under 35 U.S.C. 154(b) by 31 days.

(21) Appl. No.: 16/379,151

(22) Filed: Apr. 9, 2019

(65) Prior Publication Data
US 2019/0231536 A1 Aug. 1, 2019

Related U.S. Application Data

(63) Continuation of application No. 15/891,551, filed on Feb. 8, 2018, now Pat. No. 10,292,825, which is a continuation-in-part of application No. 15/193,149, filed on Jun. 27, 2016, now Pat. No. 10,292,834.

(51) Int. Cl.
| A61F 2/44 | (2006.01) |
| A61F 2/30 | (2006.01) |
| A61F 2/46 | (2006.01) |

(52) U.S. Cl.
CPC .......... *A61F 2/30771* (2013.01); *A61F 2/447* (2013.01); *A61F 2/4455* (2013.01); *A61F 2/4611* (2013.01); *A61F 2/4603* (2013.01); *A61F 2002/3008* (2013.01); *A61F 2002/3028* (2013.01); *A61F 2002/30166* (2013.01); *A61F 2002/30261* (2013.01); *A61F 2002/30266* (2013.01); *A61F 2002/30273* (2013.01); *A61F 2002/30281* (2013.01); *A61F 2002/30593* (2013.01); *A61F 2002/30828* (2013.01); *A61F 2002/30892* (2013.01); *A61F 2002/30904* (2013.01); *A61F 2002/4622* (2013.01); *A61F 2002/4627* (2013.01); *A61F 2002/4629* (2013.01)

(58) Field of Classification Search
CPC ..... A61F 2/44–447; A61F 2/46; A61F 2/4611
See application file for complete search history.

(56) References Cited

U.S. PATENT DOCUMENTS

| 5,425,772 | A | 6/1995 | Brantigan | |
| 5,443,514 | A | 8/1995 | Steffee | |
| 5,716,415 | A | 2/1998 | Steffee | |
| 6,224,631 | B1 | 5/2001 | Kohrs | |
| 6,290,724 | B1 * | 9/2001 | Marino | A61F 2/4455 623/17.11 |
| 6,537,320 | B1 * | 3/2003 | Michelson | A61F 2/447 623/17.11 |
| 6,942,698 | B1 | 9/2005 | Jackson | |
| 7,326,251 | B2 * | 2/2008 | McCombe | A61F 2/4611 623/17.16 |

(Continued)

*Primary Examiner* — Eduardo C Robert
*Assistant Examiner* — Michelle C Eckman

(57) ABSTRACT

Intervertebral implants, assemblies, and methods thereof. An intervertebral implant includes opposing chamfered edges to reduce a diagonal distance between the edges. The reduced diagonal distance minimizes distraction of an intervertebral disc space during insertion of the implant. A tool for insertion and rotation of the implant is also provided.

20 Claims, 7 Drawing Sheets

(56) References Cited

U.S. PATENT DOCUMENTS

| | | | |
|---|---|---|---|
| 7,331,996 B2 | 2/2008 | Sato et al. | |
| 7,396,365 B2 | 7/2008 | Michelson | |
| 7,776,094 B2 * | 8/2010 | McKinley | A61F 2/4455 623/17.16 |
| D627,468 S * | 11/2010 | Richter | D24/155 |
| 8,172,905 B2 * | 5/2012 | Baynham | A61F 2/447 623/17.16 |
| 8,591,589 B2 | 11/2013 | McCombe et al. | |
| 8,623,088 B1 * | 1/2014 | Tohmeh | A61F 2/4455 623/17.11 |
| 8,801,791 B2 * | 8/2014 | Soo | A61F 2/447 623/17.16 |
| 9,039,768 B2 * | 5/2015 | Voellmicke | A61F 2/4611 623/17.16 |
| 9,095,445 B2 | 8/2015 | Yu et al. | |
| 9,730,802 B1 * | 8/2017 | Harvey | A61F 2/4611 |
| 2006/0195190 A1 * | 8/2006 | Lechmann | A61F 2/447 623/17.11 |
| 2012/0078370 A1 * | 3/2012 | James | A61F 2/4465 623/17.16 |
| 2013/0018466 A1 * | 1/2013 | Yu | A61F 2/4455 623/17.16 |
| 2013/0090735 A1 * | 4/2013 | Mermuys | A61F 2/442 623/17.16 |
| 2014/0031941 A1 | 1/2014 | McCombe et al. | |
| 2014/0031943 A1 | 1/2014 | Yu et al. | |
| 2014/0039626 A1 * | 2/2014 | Mitchell | A61F 2/4611 623/17.16 |
| 2014/0277494 A1 * | 9/2014 | Muhanna | A61F 2/4455 623/17.16 |
| 2018/0200063 A1 * | 7/2018 | Kahmer | A61F 2/447 |
| 2019/0247197 A1 * | 8/2019 | Jagannathan | A61F 2/447 |

\* cited by examiner

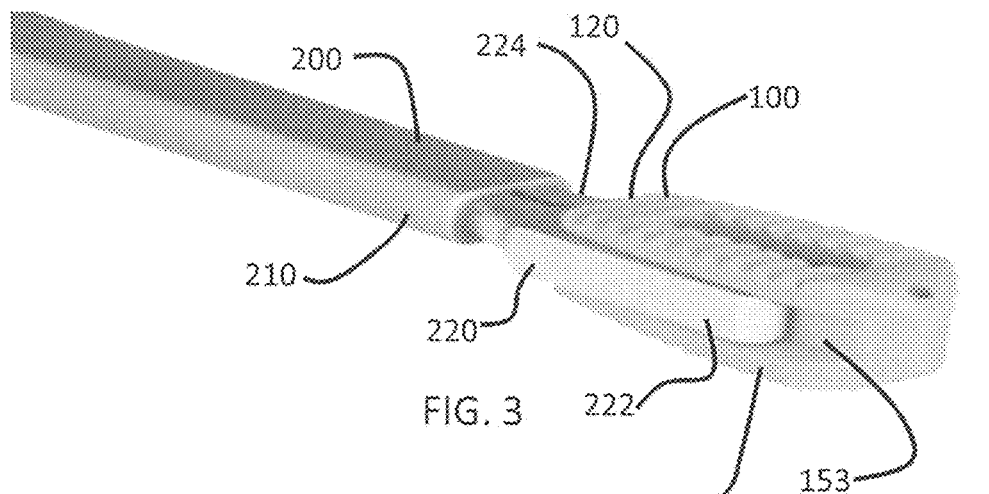
FIG. 3
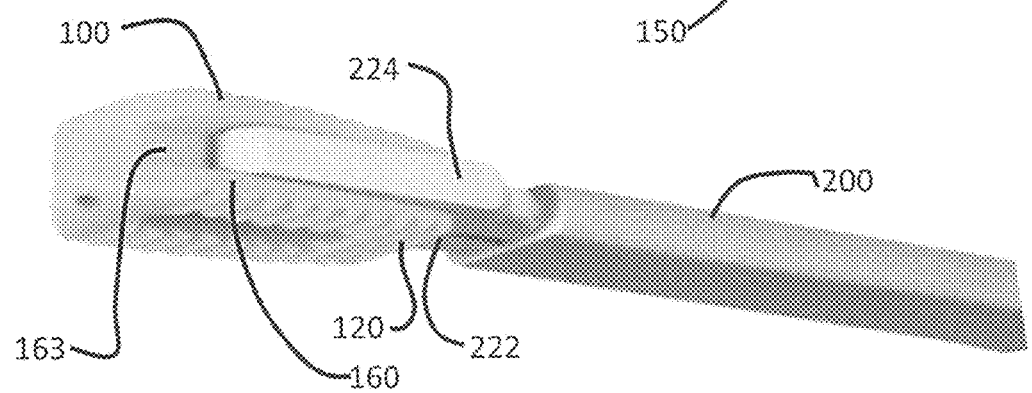
FIG. 3A
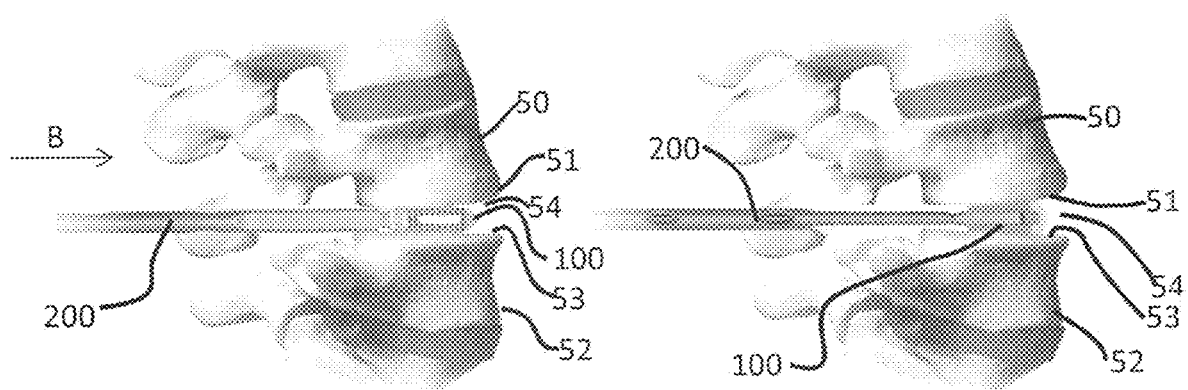
FIG. 4
FIG. 5

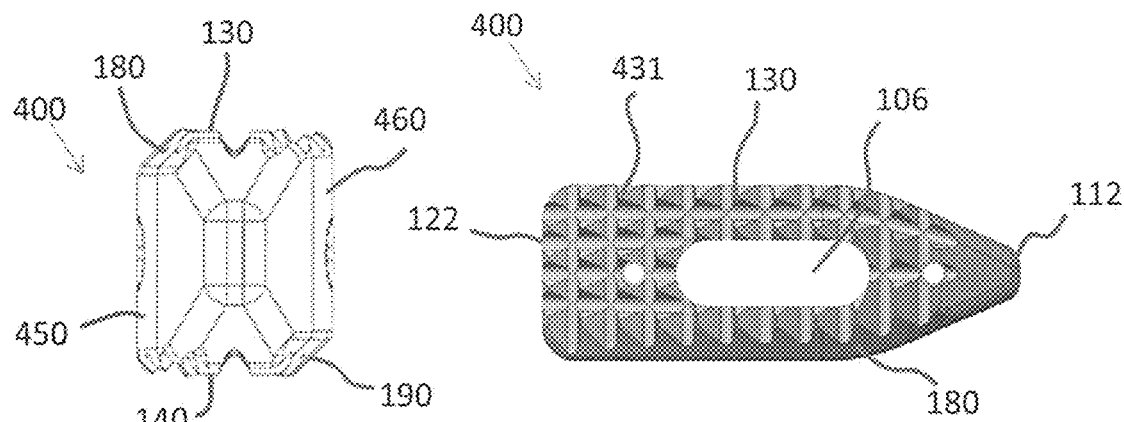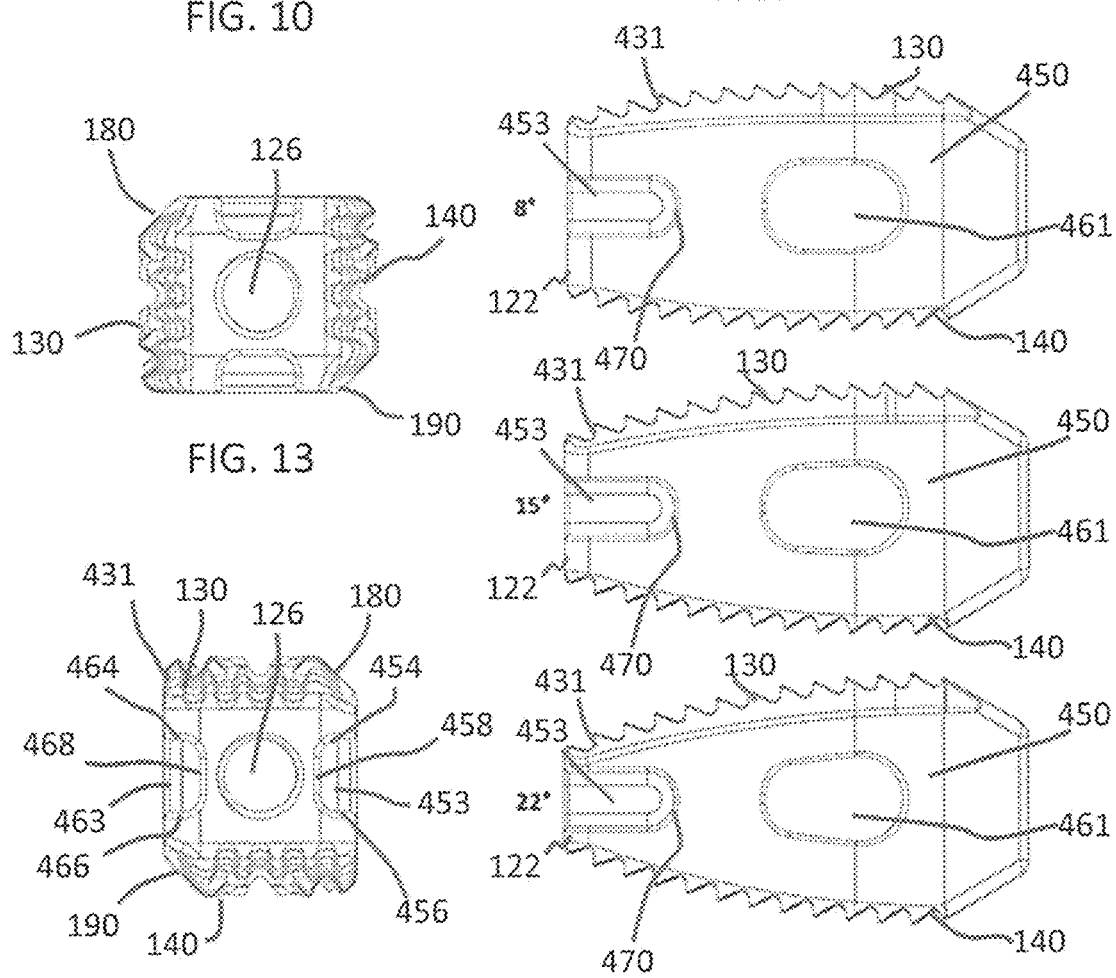
FIG. 10
FIG. 11
FIG. 13
FIG. 14
FIG. 12

INTERVERTEBRAL SPACER WITH CHAMFERED EDGES

CROSS REFERENCE TO RELATED APPLICATIONS

This application is a continuation of U.S. patent application Ser. No. 15/891,551, filed on Feb. 8, 2018, which is a continuation-in-part of U.S. patent application Ser. No. 15/193,149, filed on Jun. 27, 2016, which are incorporated by reference herein in their entireties for all purposes.

FIELD OF THE INVENTION

The present invention relates to a spinal implant and, more specifically, to a spinal implant with chamfered edges that can be inserted into a disc space and rotated in situ, reducing over-distraction of the disc space.

BACKGROUND

Implants can be inserted to perform Posterior Lumbar Interbody Fusion ("PLIF") and/or Transforaminal Lumbar Interbody Fusion ("TLIF") of a spine by inserting the implant on its side and rotating the implant in situ once the implant is located between target vertebrae. A problem associated with this technique is that the diagonal distance between opposing corners of the implant is significantly greater than the height of the implant, resulting in over-distraction of the disc space in which the implant is inserted as the implant is being rotated to its final orientation. Associated with this over-distraction is also the potential for scraping the endplates of either or both of the target vertebrae during the rotation process.

Accordingly, there exists a need for a rotatable implant that reduces over-distraction of the disc space into which the implant is inserted during rotation from an insertion position to a final position.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, an implant assembly may include a spinal implant configured to perform TLIF or PLIF procedures, for example. The assembly may also include a specially designed insertion tool for the insertion and rotation of the implant in situ after insertion of the implant into a disc space.

In one embodiment, the implant is a spacer that includes an elongate body having a central longitudinal axis extending through the body, an anterior portion having an anterior end tapering toward the longitudinal axis, and a posterior portion, distal from the anterior portion. A superior surface extends between the tapered end and the posterior end. A corresponding inferior surface also extends between the anterior end and the posterior end. A first sidewall extends between the superior surface and the inferior surface on a first side of the longitudinal axis and a second sidewall extending between the superior surface and the inferior surface on a second side of the longitudinal axis. An intersection of the first sidewall and the superior surface comprises a first chamfered edge and an intersection of the second sidewall and the inferior surface comprises a second chamfered edge.

In an alternative embodiment, the implant is a spacer that includes an elongate body having a central longitudinal axis extending through the body, an anterior portion having an anterior end, and a posterior portion, distal from the anterior portion. A superior surface extends between the anterior end and the posterior end and an inferior surface extends between the anterior end and the posterior end. A first sidewall extends between the superior surface and the inferior surface on a first side of the longitudinal axis and a second sidewall extends between the superior surface and the inferior surface on a second side of the longitudinal axis. A first diagonal distance between an intersection of the first sidewall and the superior surface an intersection of the second sidewall and the inferior surface is less than a second diagonal distance between an intersection of the first sidewall and the inferior surface and an intersection of the second sidewall and the superior surface.

In still another alternative embodiment, an implant assembly includes the spacer described above and an insertion tool. The insertion tool is removably attachable to the implant and is adapted to insert the implant between adjacent discs. The insertion tool includes a handle and a gripper extending distally from the handle. The gripper has a first fork and a second fork extending generally parallel to the first fork. A gap is provided between the first fork and the second fork. The gap is sized to allow the first fork to be inserted along a longitudinal indentation in the first wall and to allow the second fork to be inserted along a longitudinal indention in the second sidewall.

According to another embodiment, a system comprises an implant and an insertion tool. The implant having an elongate body having a central longitudinal axis extending through the body; an anterior portion and a posterior portion, the posterior portion having an internally threaded opening; a superior surface extending between the anterior portion and the posterior portion; an inferior surface extending between the anterior portion and the posterior portion; a first sidewall extending between the superior surface and the inferior surface on a first side of the longitudinal axis; and a second sidewall extending between the superior surface and the inferior surface on a second side of the longitudinal axis, the first sidewall and the second sidewall comprising a first indentation and a second indentation, respectively, proximate the posterior portion, wherein an intersection of the first sidewall and the superior surface comprises a first chamfered edge and wherein an intersection of the second sidewall and the inferior surface comprises a second chamfered edge. The insertion tool having a gripper extending distally from the handle, the gripper having a first fork and a second fork extending generally parallel to the first fork, wherein a gap is provided between the first fork and the second fork, the gap being sized to allow the first fork to be inserted into the first indentation and the second fork into the second indention. The insertion tool is removably attachable to the implant and adapted to insert the implant between adjacent vertebrae in a first orientation with the first and second sidewalls configured to contact the adjacent vertebrae and rotating the implant 90° to a second orientation with the superior and inferior surfaces configured to contact the adjacent vertebrae.

According to yet another embodiment, a system comprises an implant and an insertion tool. The implant having an elongate body having a central longitudinal axis extending through the body; an anterior portion and a posterior portion, the posterior portion having an internally threaded opening; a superior surface extending between the anterior portion and the posterior portion; an inferior surface extending between the anterior portion and the posterior portion; a first sidewall extending between the superior surface and the inferior surface on a first side of the longitudinal axis; and a second sidewall extending between the superior surface and the inferior surface on a second side of the longitudinal axis, the first sidewall and the second sidewall comprising a first indentation and a second indentation, respectively, proximate the posterior portion, wherein the first indentation includes a superior sidewall surface, an inferior sidewall surface, and a side surface extending between and connecting the respective superior sidewall surface and the inferior sidewall surface, the superior sidewall surface and the side surface being connected with a first curved portion and the side surface and the inferior sidewall surface being connected with a second curved portion, wherein the first indentation terminates at a curved wall such that the wall connects the superior sidewall surface and the inferior side wall surface with a semi-circular configuration, wherein an intersection of the first sidewall and the superior surface comprises a first chamfered edge and wherein an intersection of the second sidewall and the inferior surface comprises a second chamfered edge. The insertion tool having a gripper extending distally from the handle, the gripper having a first fork having a curved portion configured to mate with the curved wall of the first indentation. The insertion tool is removably attachable to the implant and adapted to insert the implant between adjacent vertebrae in a first orientation with the first and second sidewalls configured to contact the adjacent vertebrae and rotating the implant 90° to a second orientation with the superior and inferior surfaces configured to contact the adjacent vertebrae.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 3 is a top perspective view of the spacer shown in FIG. 1 attached to an exemplary insertion tool;

FIG. 3A is a bottom perspective view of the spacer shown in FIG. 1 attached to the insertion tool shown in FIG. 3;

FIG. 4 is a side elevational view of the spacer shown in FIG. 1 being inserted into an intervertebral space prior to rotating;

FIG. 5 is a side elevational view of the spacer shown in FIG. 1 being inserted into an intervertebral space after rotating;

FIG. 10 is a front view of a spacer according to a third exemplary embodiment;

FIG. 11 is a top view of the spacer shown in FIG. 10;

FIG. 12 is a series of three side views of spacer designs having different degrees of lordosis;

FIG. 13 is a back view of the spacer shown in FIG. 10 as intended to be first positioned in the disc space;

FIG. 14 is a back view of the spacer as shown in FIG. 13 after being rotated 90° and into final position in the disc space;

DETAILED DESCRIPTION

Figure 1:
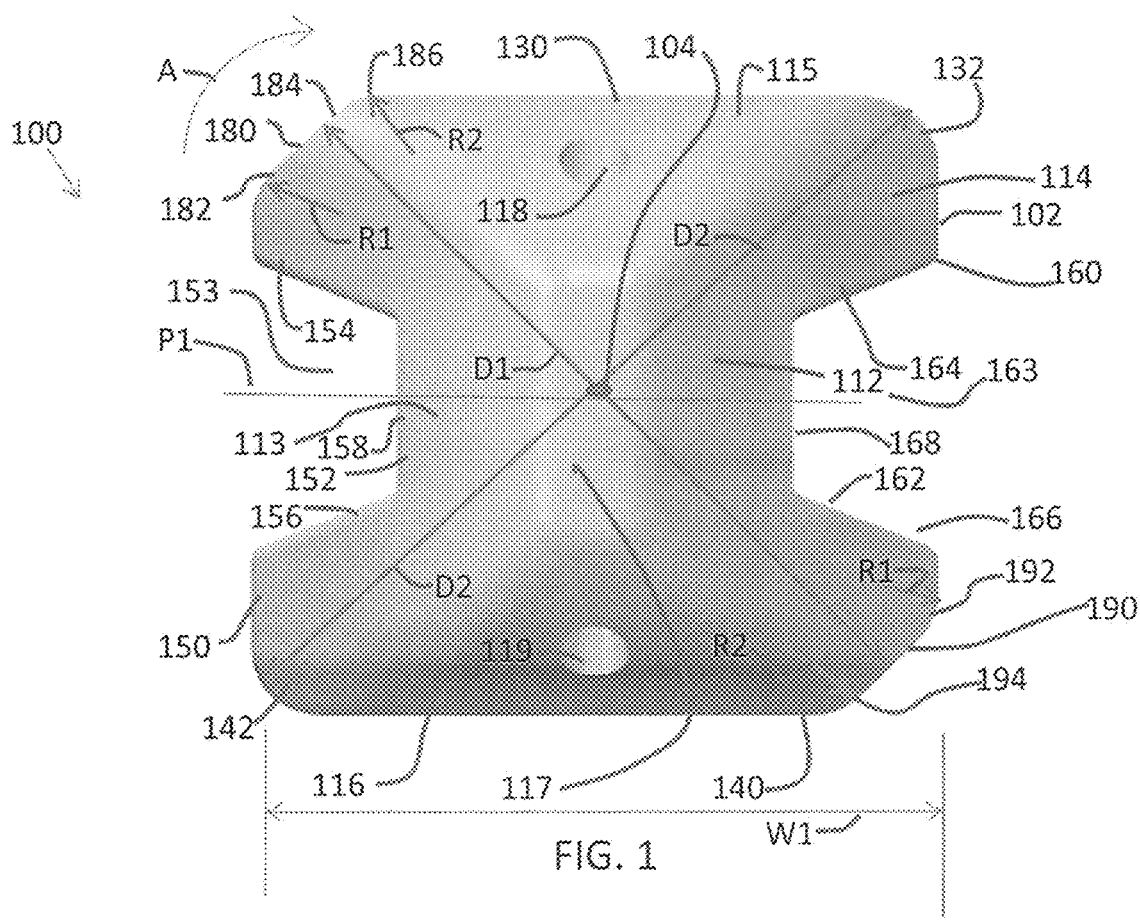
FIG. 1 is a front view of a spacer according to a first exemplary embodiment.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present disclosure provides embodiments of spinal implants that can be inserted into a disc space sideways and rotated 90 degrees in situ without overly distracting the disc space.

According to one embodiment, as shown in FIGS. 1-3A, an implant in the form of a spacer 100 is shown. As shown in FIGS. 4 and 5, spacer 100 is inserted into an intervertebral space 54 between a superior vertebral member 50 and an inferior vertebral member 52. Spacer 100 can be formed from biocompatible materials, such as, but not limited to, polyetheretherketone (PEEK), titanium, titanium alloys, other surgical grade metals, alloys, or a combination thereof.

Referring back to FIGS. 1 and 2, spacer 100 includes an elongate body 102 having a central longitudinal axis 104 extending through body 102. Optionally, body 102 includes a graft window or through-space 106 extending generally centrally therethrough. Through-space 106 may be provided to allow for the insertion of graft material (not shown) and/or to allow for the ingrowth of bone from either or both of vertebral members 50, 52.

Body 102 includes an anterior portion 110 that has an anterior end 112 tapering toward longitudinal axis 104. Anterior portion 110 has a maximum width W1 that is orthogonal to longitudinal axis 104. Anterior end 112 includes a first side wall 113 that extends obliquely toward longitudinal axis 104 and a second side wall 114 that extends obliquely toward longitudinal axis 104. Additionally, anterior end 112 also includes a superior surface 115 that extends obliquely toward longitudinal axis 104 and an inferior surface 116 that extends toward longitudinal axis 104.

The convergence of walls 113, 114 and surfaces 115, 116 forms a blunt tip 117 that enhances the ability of the implanting surgeon to insert tip 117 into intervertebral space 54 to maneuver the spacer 100 into a desired position. Further, all of walls 113, 114 and surfaces 115, 116 are generally smooth and free of any teeth, ribs, or ridges so as not to scrape endplates 51, 53 of superior vertebral member 50 and inferior vertebral member 52, respectively, during insertion of spacer 100 into intervertebral space 54. Additionally, all or some of walls 113, 114 and surfaces 115, 116 can be generally flat or convex in shape with rounded edges.

Optionally, superior surface 115 and inferior surface 116 can include openings 118, 119, respectively, formed therein. Openings 118, 119 can be separate openings or opposing sides of a single opening that passes through anterior end 112. Openings 118, 119 can be used for the optional insertion of a radiopaque marker (not shown), if desired.

A posterior portion 120 is located distal from anterior portion 110. Posterior portion 120 includes a generally straight side 122. Optionally, a through-opening 124 extends through posterior end 120. Opening 124 can be used for the optional insertion of a radiopaque marker (not shown), if desired.

Posterior end 120 has a minimum width W2 that is orthogonal to longitudinal axis 104 such that minimum width W2 is less than maximum width W1. Body 102 can taper from maximum width W1 down to minimum width W2 from anterior portion 110 to posterior portion 120. Thus, width W2 may be generally smaller than width W1. In the alternative, width W2 may be substantially the same as width W1 or width W2 may be larger than width W1.

A superior surface 130 extends between tapered end 112 and posterior end 120. Similarly, an inferior surface 140 also extends between anterior end 112 and posterior end 120. Each of superior surface 130 and inferior surface 140 may be generally planar. In the alternative, the superior and inferior surfaces 130, 140 may be curved or tapered to align with the natural anatomy of the adjacent vertebral members 50, 52. The superior and inferior surfaces 130, 140 may each include a plurality of lateral teeth 131 at posterior portion 120 and a portion of anterior portion 110, although tapered anterior end 112 may form a nose portion substantially free of teeth 131. Teeth 131 are used to grip inferior endplate 51 on superior vertebral member 50 and superior endplate 53 on inferior vertebral member 52.

A first sidewall 150 extends between superior surface 130 and inferior surface 140 on a first side 152 of longitudinal axis 104 and, similarly, a second sidewall 160 extends between superior surface 130 and inferior surface 140 on a second side 162 of longitudinal axis 104. The teeth 131 on the superior and inferior surfaces 130, 140 may extend at least along a portion between the first and second sidewalls 150, 160, except where interrupted by the through-space 106 and where chamfered to avoid scraping during rotation. Each sidewall 150, 160 can be slightly convex in shape or substantially planar in shape, for example. In one embodiment each sidewall 150, 160 extends at an angle at least slightly oblique relative to longitudinal axis 104, which results in posterior width W2 being less than anterior width W1 so that, as spacer 100 is rotated between vertebral members 50, 52, only the portion of spacer 100 proximate to width W1 engages and scrapes endplates 51, 53 during rotation.

Additionally, sidewalls 150, 160 are generally smooth, without teeth, so that spacer 100 can easily slide along inferior vertebral member 52 and superior vertebral member 50, respectively, during insertion of spacer 100 into intervertebral space 54.

As shown in FIG. 1, the superior surface 130 comprises a first chamfered edge 180 and the inferior surface 140 comprises a second chamfered edge 190. For example, an intersection of first sidewall 150 and superior surface 130 may include first chamfered edge 180, and an intersection of second sidewall 160 and inferior surface 140 may include a second chamfered edge 190. The chamfered edges 180, 190 may interrupt the teeth 131 on the superior and inferior surfaces 130, 140 at diagonal corners relative to one another in order to reduce the maximum distance therebetween. Chamfered edges 180, 190 may each extend the length of body 102 between anterior end 112 to posterior portion 120. In the alternative, chamfered edges 18, 190 may extend along a portion of the length of the body 102 between the anterior end 112 and the posterior portion 120.

First and second chamfered edges 180, 190 may be substantially planar (i.e., beveled) or may have other configurations. For example, the first chamfered edge 180 may include a first arcuate portion 182 having a radius R1, a linear portion 184 attached to first arcuate portion 182, and a second arcuate portion 186 attached to linear portion 184, distal from first arcuate portion 182. Second arcuate portion 186 has a radius R2, which may or may not be the same as radius R1.

Across a first diagonal distance D1 from first chamfered edge 180, inferior surface 140 comprises second chamfered edge 190. Second chamfered edge 190 may be substantially planar (i.e., beveled) or may have other configurations. For example, the second chamfered edge 190 may include a first arcuate portion 192 having a radius R1, a linear portion 194 attached to first arcuate portion 190, and a second arcuate portion 196 attached to linear portion 194, distal from first arcuate portion 192. Second arcuate portion 196 has a radius R2, which may or may not be the same as radius R1. The distance D1 between the first chamfered edge 190 and the second chamfered edge 190 is minimized, which preferably lessens contact of the spacer 100 when rotated into position in the vertebral disc space.

While chamfered edges 180, 190 are shown to form edges that provide a reduced diagonal, those skilled in the art will recognize that edges 180, 190 can be formed in other manners, such as, for example, by beveling or filleting, such that first diagonal distance D1 is reduced from a diagonal formed with non-chamfered, non-beveled, or non-filleted opposing edges.

Figure 2:
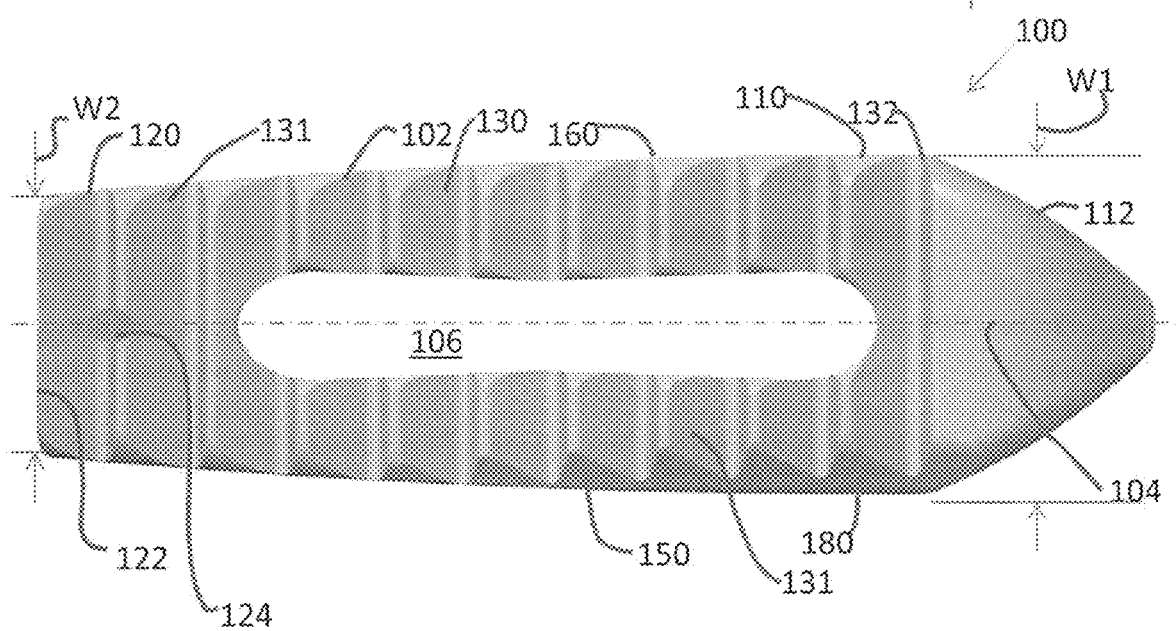
FIG. 2 is a top elevational view of the spacer shown in FIG. 1.

At least some of the plurality of laterally extending teeth 131 on both superior surface 130 and inferior surface 140 may end prior to chamfered edges 180, 190 to reduce the risk of scraping endplates 51, 53 of superior vertebral member 50 and inferior vertebral member 52, respectively, during insertion of spacer 100 into intervertebral space 54 and subsequent rotation. As shown in FIG. 2, teeth 131 taper inwardly toward longitudinal axis 104 to further ameliorate scraping risk. The degree of taper or chamfer 180, 190 may be greatest at anterior portion 110 and the degree of taper or chamfer 180, 190 may lessen towards posterior end 120. In addition, the volume of chamfer 180, 190 may be largest for the first tooth at the anterior portion 110 and reduce in volume towards the posterior end 120. In other words, the greatest degree of chamfer 180, 190 may occur proximate to the anterior portion 110.

An intersection of first sidewall 150 and inferior surface 140 forms a corner 142 and an intersection of second sidewall 160 and superior surface 120 forms a corner 132. Optionally, each of corners 142, 132 can also be tapered or rounded to reduce the risk of scraping endplates 51, 53 for vertebral members 50, 52, respectively, during insertion of spacer 100 into intervertebral space 54. These corners 132, 142 may also extend substantially along the length of the spacer 100. A second diagonal distance between corners 142, 132 is shown in FIG. 1 as diagonal D2 such that first diagonal distance D1 is at least less than a second diagonal distance D2. Thus, the distance D1 is preferably smaller than the distance D2 to reduce scraping of the endplates during rotation.

With first diagonal distance D1 being less than second diagonal distance D2, spacer 100 can be rotated in a direction indicated by curved arrow A in FIG. 1 (clockwise as shown in FIG. 1) during insertion of spacer 100 into intervertebral space 54, which results in less distraction of vertebral members 50, 52 than if spacer 100 were to be rotated in a direction opposite arrow A (counter-clockwise as shown in FIG. 1).

Each of first sidewall 150 and second sidewall 160 comprises a longitudinal indentation 153, 163, respectively. Indentations 153, 163 may be generally concave recesses cut into the sidewalls 150, 160 of the spacer 100. Instead of being arcuate, these concave recesses may have generally flat and angular sections. For example, indentation 153 may be segmented with generally planar sidewalls including a superior sidewall surface 154, an inferior sidewall surface 156, and a side surface 158 extending between and connecting the respective superior sidewall surface 154 and the respective inferior sidewall surface 156. The superior sidewall surface 154 may connect to side surface 158 via a first generally obtuse angle (e.g., an angle greater than 90°). Similarly, the inferior sidewall surface 156 may connect to side surface 158 via a second generally obtuse angle (e.g., an angle greater than 90°). Although obtuse angles are shown, it is contemplated that the sidewall surfaces 154, 156 may connect with the side surface 158 at right angles or acute angles. Optionally, as shown in FIG. 1, each of superior sidewall surface 154 and inferior sidewall surface 156 extends at an oblique angle relative to a central horizontal plane P1 (extending normally out of the plane of the paper of FIG. 1), forming a tapered indentation 153.

Similarly, indentation 163 is segmented with generally planar sidewalls including a superior sidewall surface 164, an inferior sidewall surface 166, and a side surface 168 extending between and connecting the respective superior sidewall surface 164 and the respective inferior sidewall surface 166. Similar to indentation 153, the superior sidewall surface 164 may connect to side surface 168 via a first generally obtuse angle (e.g., an angle greater than 90°). Similarly, the inferior sidewall surface 166 may connect to side surface 168 via a second generally obtuse angle (e.g., an angle greater than 90°). Although obtuse angles are shown, it is contemplated that the sidewall surfaces 164, 166 may connect with the side surface 168 at right angles or acute angles. In addition, each of superior sidewall surface 164 and inferior sidewall surface 166 may extend at an oblique angle relative to central horizontal plane P1 (extending normally out of the plane of the paper of FIG. 1), forming a tapered indentation 163.

Indentations 153, 163 are provided to support an insertion tool 200 (shown in FIGS. 3-5) that is removably attachable to spacer 100 and is adapted to insert spacer 100 between adjacent vertebral members 50, 52. Insertion tool 200 includes a handle 210 and a gripper 220 extending distally from handle 210.

Gripper 220 has a first fork 222 and a second fork 224 extending generally parallel to first fork 222, such that a gap is provided between first fork 222 and second fork 224. The gap is sized to allow first fork 222 to be inserted along longitudinal indentation 153 in first sidewall 150 of spacer 100 and to allow second fork 224 to be inserted along longitudinal indention 163 in second sidewall 160. Optionally, forks 222, 224 can have a tapered cross-section that mates with the tapered cross-section of indentations 153, 163, respectively. Alternatively, forks 222, 224 can have a different cross-section, as long as forks 222, 224 can securely grip spacer 100 for insertion into intervertebral space 54.

Optionally, first fork 222 is biased toward second fork 224 so that gripper 220 securely grips spacer 100 during the insertion process. Additionally, when insertion tool 200 is attached to spacer 100, insertion tool 200 is adapted to insert spacer 100 between adjacent vertebral members 50, 52 and to rotate spacer 100 about ninety degrees about longitudinal axis 104 of spacer 100 from the position shown in FIG. 4 to the position shown in FIG. 5.

First and second forks 222, 224 may be positioned in respective longitudinal indentations 153, 163 such that the forks 222, 224 span a longitudinal distance along the indentations 153, 163. For example, the first and second forks 222, 224 may span more than half way, but less than the entire length of the implant 100. The forks 222, 224 may be sized and configured such that the opposite side surfaces of the respective forks 222, 224 contact and engage the superior sidewall surfaces 154, 164 and inferior sidewall surfaces 156, 166 of the respective indentations 153, 163. Similarly, a bottom surface of each respective fork 222, 224 mates with and contacts the side surfaces 158, 168 of the indentations 153, 163. In this manner, the forks 222, 224 may be respectively received in the indentations 153, 163 such that the forks do not form an outer surface of the spacer 100 and do not necessarily contact the vertebral endplates during insertion or rotation of the spacer 100. Thus, the forks 222, 224 do not cam open or other increase the distance of the intervertebral disc space during insertion or rotation of the spacer 100 into its final position. Optionally, each of first fork 222 and second fork 224 is laterally disposed within the respective longitudinal indentation 153, 163 so that, as spacer 100 is being rotated from the position shown in FIG. 4 to the position shown in FIG. 5, neither fork 222, 224 inadvertently scrapes either vertebral member 50, 52 (i.e., spacer sidewalls 150, 160 extend laterally outwardly of forks 222, 224 so that sidewall 150, 160, and not forks 222, 224, engage vertebral members 50, 52).

To implant spacer 100 into intervertebral space 54, spacer 100 is removably attached to tool 200 as shown in FIGS. 3 and 4. First fork 222 is slid into indentation 153 and second fork 224 is slid into indentation 163 from posterior portion 120. Spacer 100 is then inserted into intervertebral space 54 in the direction of arrow "B", as shown in FIG. 4. The taper of anterior end 112 allows the inserting physician to generally locate spacer 100 in intervertebral space 54 and to advance spacer 100 anteriorly in vertebral space 54. The smooth sidewalls 150, 160 allow spacer 100 to slide along endplates 51, 53 of superior vertebral members 50, 52, respectively, with minimal friction.

When spacer 100 is located in a desired position, tool 200 is rotated 90 degrees, thereby rotating spacer 100 90 degrees as well, in the direction of arrow "A" in FIG. 1, to the position shown in FIG. 5. Chamfered edges 180, 190 reduce distraction between vertebral members 50, 42 as spacer 100 is rotated. Teeth 131 on superior surface 130 and inferior surface 140 grip endplates 51, 53, respectively, to reduce potential movement of spacer 100 between intervertebral members 50, 52.

An alternative embodiment of an implant, or spacer, 300 ("spacer 300") is shown in FIGS. 6-9. Elements in spacer 300 that are identical to elements in spacer 100 are given the same reference numbers as those used for spacer 100. Spacer 300 is similar to spacer 100 except that, in addition to first and second diametrically opposed chamfered edges 180, 190, spacer 300 also includes a third chamfered edge 380 formed on inferior surface 340 (e.g., at an intersection of a first sidewall 350 and an inferior surface 340) as well as a fourth chamfered edge 390 on the diagonal opposite of the superior surface 330 (e.g., at an intersection of a second sidewall 360 and a superior surface 330). The four chamfered edges 180, 380, 190, 390 result in generally equal length diagonals, thereby allowing for spacer 300 to be rotated either clockwise or counterclockwise about a longitudinal axis 304 without overly distracting adjacent vertebral members 50, 52 and/or causing scraping of the vertebral members 50, 52. In this embodiment, due to the presence of four chamfered edges 180, 190, 380, 390 the area of each respective chamfer 180, 190, 380, 390 may be less than in the embodiment shown in FIGS. 1-2 with only two diagonal chamfers 180, 190 in order to maximize the contact area of the superior and inferior surfaces 330, 340 with the vertebral endplates 50, 52.

Chamfered edges 180, 190, 380, 390 may extend along spacer 300 between anterior portion 310 and posterior portion 320 or a portion thereof. Teeth 331 on each of superior surface 330 and inferior surface 340 may extend at least along a portion of spacer 300 between the first and second sidewalls 350, 360, except where interrupted by the through-space 306 and where chamfered at chamfered edges 180, 190, 380, 390 to avoid scraping during rotation. The degree of taper or chamfer 180, 190, 380, 390 may be greatest at anterior portion 310 and the degree of taper or chamfer 180, 190, 380, 390 may lessen towards posterior end 320. In addition, the volume of chamfer 180, 190, 380, 390 may be largest for the first tooth at the anterior portion 310 and reduce in volume towards the posterior end 320. In other words, the greatest degree of chamfer 180, 190, 380, 390 may occur proximate to the anterior portion 310.

Figure 8:
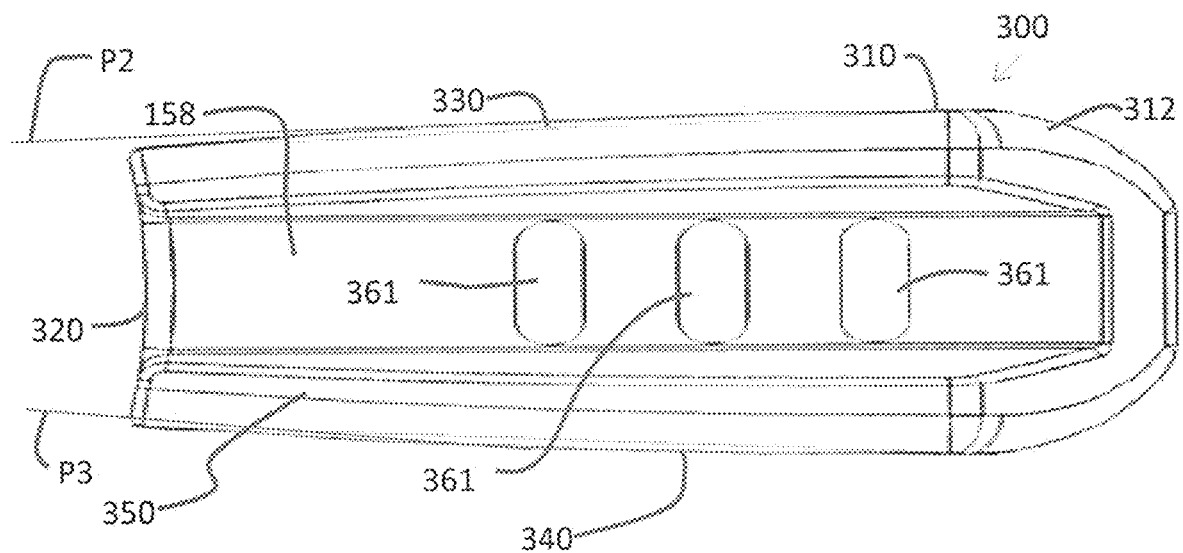
FIG. 8 is a side elevational view of the spacer shown in FIG. 6

Also, optionally, as shown in FIG. 8, superior surface 330 extends in a first plane P2 extending perpendicularly from the plane of the paper of FIG. 8 and inferior surface 340 extends in a second plane P3, extending perpendicularly from the plane of the paper of FIG. 8, oblique to the first plane P2 to conform with natural spacing between adjacent vertebral members 50, 52. It will be appreciate that these planes P2, P3 may be generally parallel, may be curved, or may increase in height toward the posterior end 320 if desired.

Further, anterior portion 310 has a widest portion having width W1 that is orthogonal to longitudinal axis 304 and posterior portion 320 has a narrowest portion W2 that is orthogonal to longitudinal axis 304, with width W2 being smaller than with W1 so that, as spacer 300 is rotated about longitudinal axis 304 during insertion, only anterior portion 310 needs to contact and distract intervertebral members 50, 52. Those skilled in the art however, will recognize that width W2 may be greater than or equal to width W1.

Figure 6:
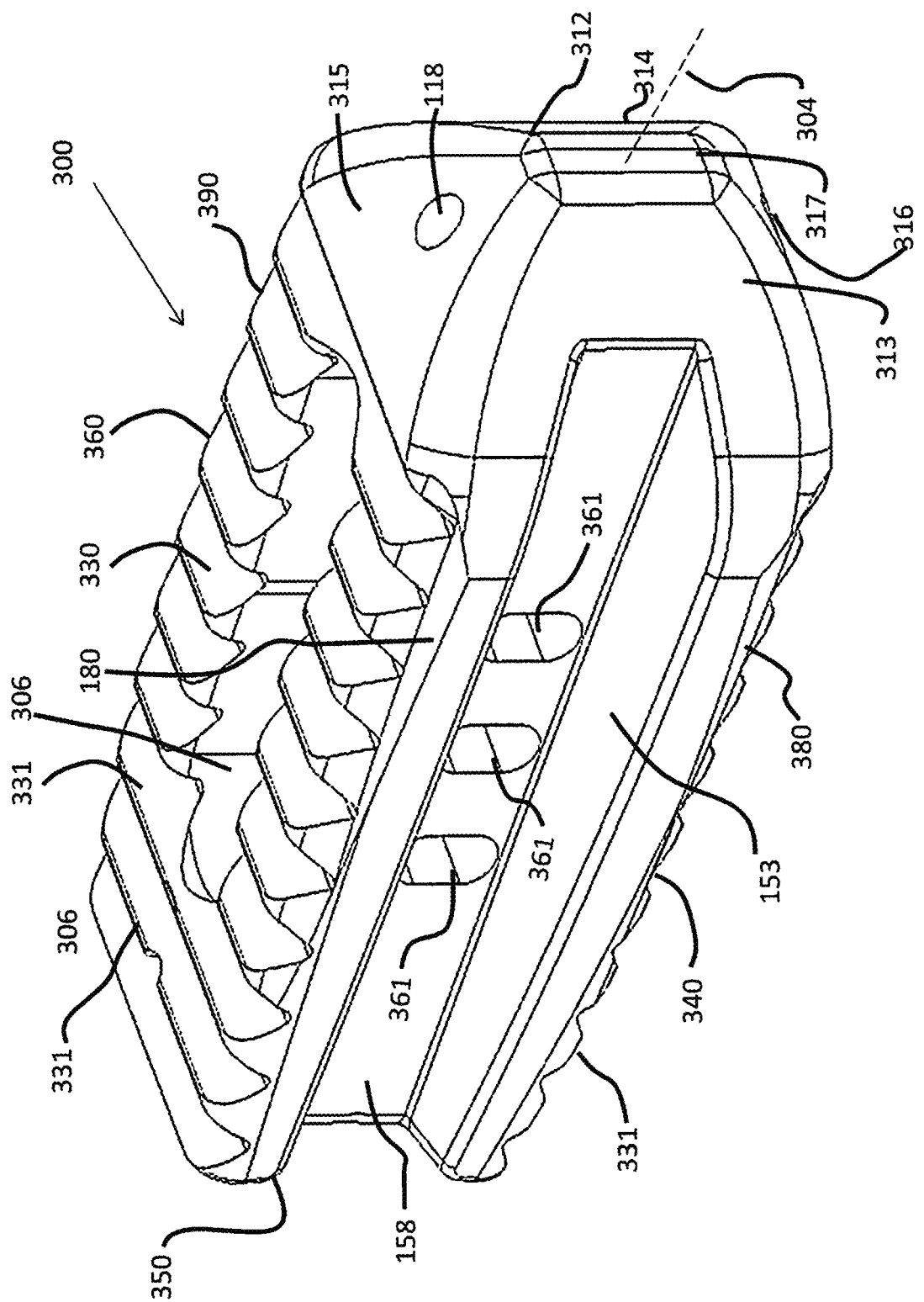
FIG. 6 is a perspective view of a spacer according to a second exemplary embodiment.
Figure 7:
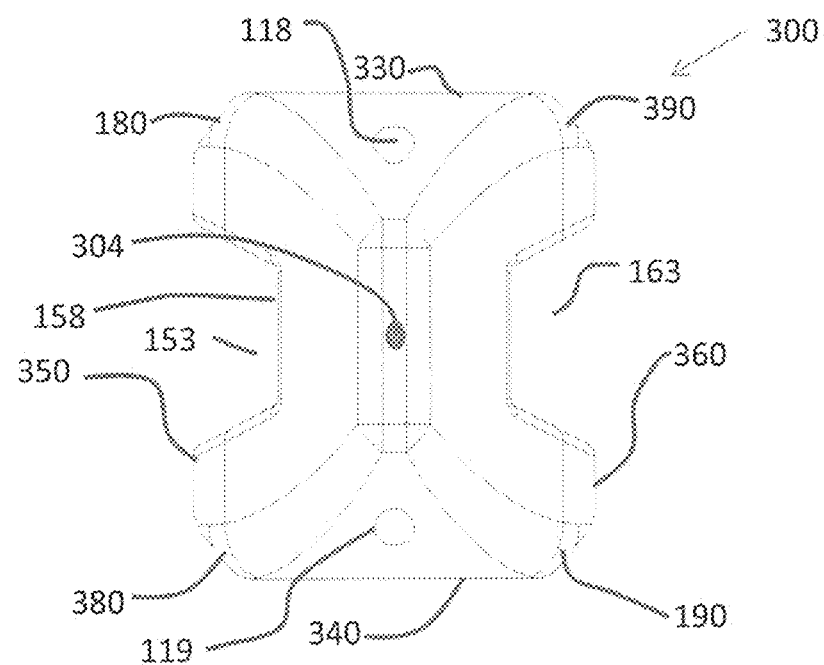
FIG. 7 is a front elevational view of the spacer shown in FIG. 6.
Figure 9:
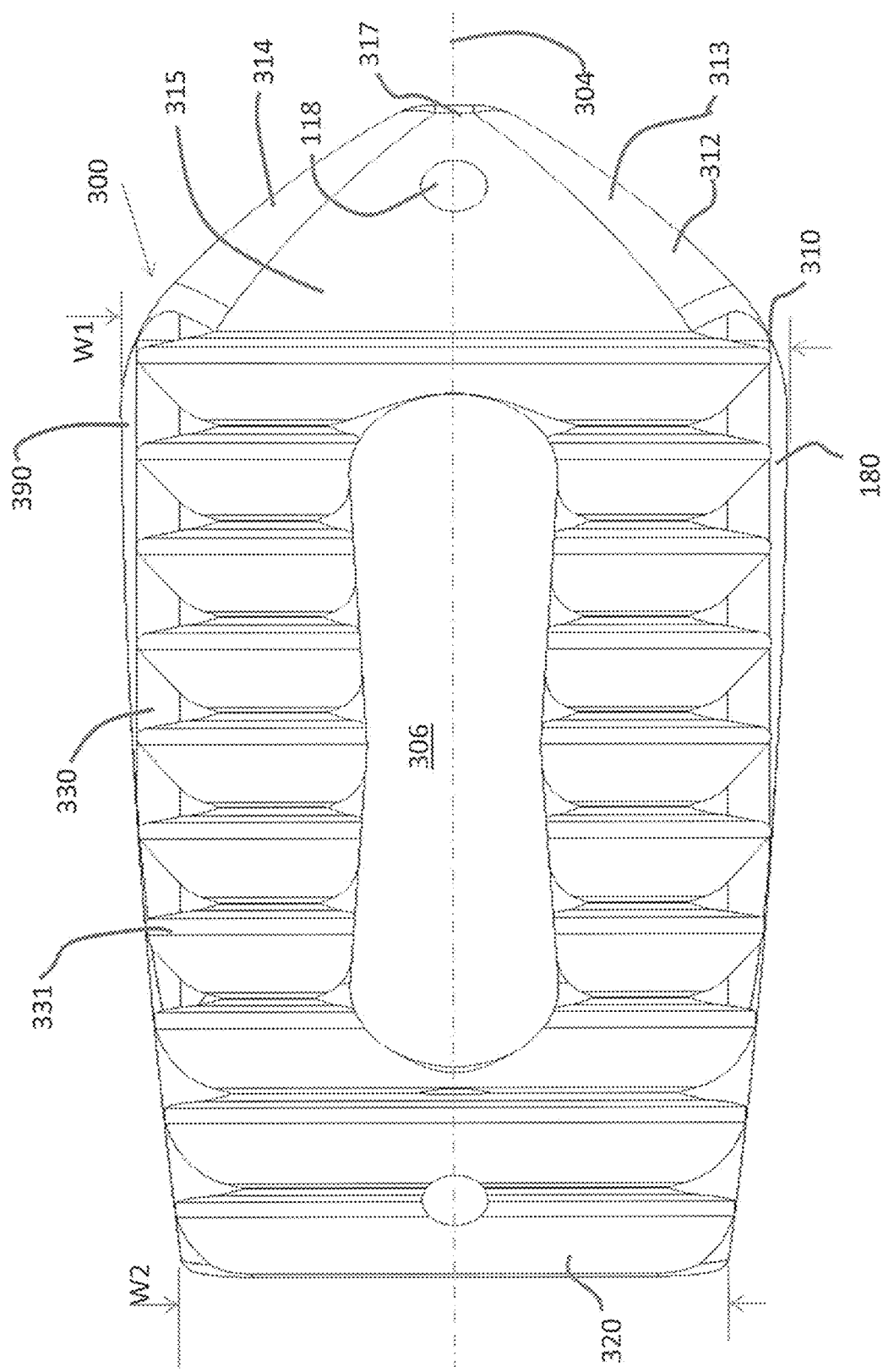
FIG. 9 is a top plan view of the spacer shown in FIG. 6.

Additionally, as shown in FIGS. 6 and 9, side surface 158 may include one or more graft holes 361 in fluid communication with through-space 306. The graft holes 361 may extend from the side surface 158 to the opposite side surface 168 of the indentations 153, 163, respectively. The graft holes 361 may include three graft holes 361 central positioned along the side surfaces 158, 168. As best seen in FIG. 8, the graft holes 361 may be generally elongate in dimension having a length greater than a width. The elongate graft holes 361 may be oriented such that they generally extend from the superior sidewall surface 154 to inferior sidewall surface 156 of indentation 153 and from the superior side wall surface 164 to the inferior sidewall surface 166 of indentation 163. For example, the elongate graft holes 361 may be oriented such that the longer portion of the graft hole 361 is generally perpendicular to the longitudinal axis of the body of the spacer 300. The graft holes 361 may allow for interdigitation of the graft material (not shown) into the disc space after spacer 300 is implanted.

An alternative embodiment of an implant, or spacer, 400 ("spacer 400") is shown in FIGS. 10-14. Elements in spacer 400 that are identical to elements in spacer 100 are given the same reference numbers as those used for spacer 100. Spacer 400 is similar to spacer 100 except that the plurality of lateral teeth 131 are replaced with individual pyramidal teeth 431, the sidewalls 450, 460 are reconfigured, and there is a different connection mechanism with the insertion tool 500.

As best seen in FIG. 11, the superior and inferior surfaces 130, 140 of the spacer 400 include a plurality of teeth 431. The plurality of teeth 431 include individual, discrete, spaced-apart teeth that may be generally uniformly shaped and dimensioned. The teeth 431 may have a generally pyramidal-shaped. The surface formed from the tip to the base facing the first and second side walls 450, 460 may be generally equidistant, and the surface from the tip to the base facing the anterior end 112 may be longer than the surface from the tip to the base facing the posterior end 122. This configuration for the teeth 431 may help the spacer 400 to resist expulsion and provide stability. Similar to teeth 131, portions of teeth 431 may be removed by chamfered edges 180, 190, for example, to facilitate rotation of the spacer 400 in situ. These chamfered edges 180, 190 or bevels on opposite corners of the spacer 400 allow for easier rotation while also minimizing over-distraction. In this configuration, the implant 100 includes bevel 180, 190 on opposite corners of the spacer's profile. The bevel cuts away an otherwise sharp corner from the spacer 400, and allows for smoother rotation in the disc space.

The sidewalls 450, 460 may include indentations 453, 463 proximate to the posterior end 122 of the spacer 400. Each of the indentations 453, 463 may be in the form of a recess extending a distance towards the anterior end 112. As best seen in FIG. 14, the indentation 453 may be segmented with a superior sidewall surface 454, an inferior sidewall surface 456, and a side surface 458 extending between and connecting the respective superior sidewall surface 454 and the respective inferior sidewall surface 456. The superior sidewall surface 454 and the side surface 458 may be connected with a first curved portion and the side surface 458 and the inferior sidewall surface 456 may be connected with a second curved portion. Similarly, indentation 463 may have the same configuration for superior sidewall surface 464, inferior sidewall surface 466, and side surface 468. As best seen in FIG. 12, the indentations 453, 463 may terminate at a wall 470 (indentation 453 is shown and indentation 463 is identical). Wall 470 may be curved such that it connects the superior sidewall surface 454, 464 and the inferior side wall surface 456, 466 with a semi-circular configuration (e.g., a half circular arc). This semi-circular configuration may be configured to receive and/or mate with a corresponding portion of an instrument (e.g., forks 222, 224 described in more detail below for instrument 500).

Additionally, as shown in FIG. 12, sidewalls 450, 460 (sidewall 450 is shown and sidewall 460 is identical) may include one or more graft holes 461 in fluid communication with through-space 106 extending therethrough. The graft holes 461 may extend from the sidewall 450 to the opposite sidewall 460. The graft holes 461 may include a single graft hole 461 centrally positioned between the superior and inferior surfaces 130, 140. The graft hole 461 may be generally elongate in dimension having a width greater than a height. The elongate graft hole 461 may be oriented such that the longer portion of the graft hole 461 is generally parallel to the longitudinal axis of the body of the spacer 400. The graft hole 461 may also be generally aligned along a longitudinal axis with the indentations 453, 463.

FIG. 12 also shows three spacer configurations at 8 degrees, 15 degrees, and 22 degrees, respectively. The side views of spacer 400 show three different degrees of lordosis, but it is envisioned that other configurations (e.g., parallel, non-parallel, curved, tapered) between the superior and inferior surfaces 130, 140 may be provided based on the clinical need.

Figure 15:
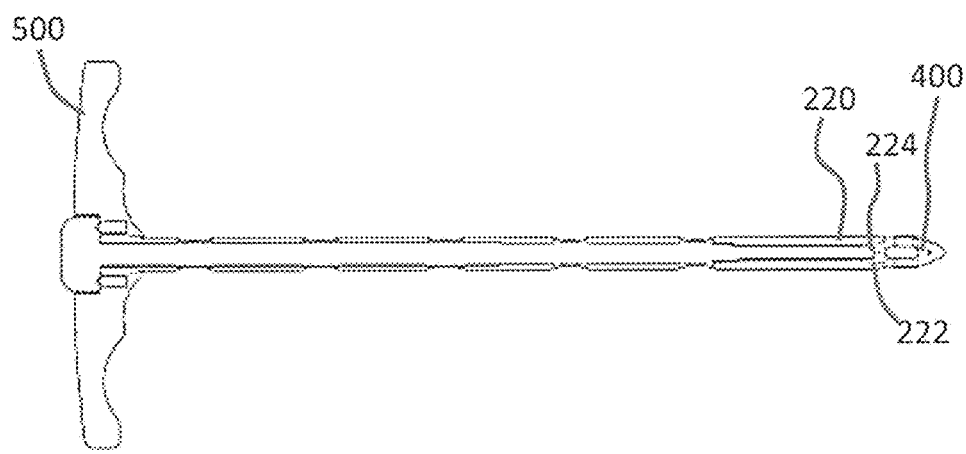
FIG. 15 is an inserter that may be used to install the spacer shown in FIG. 10.
Figure 16:
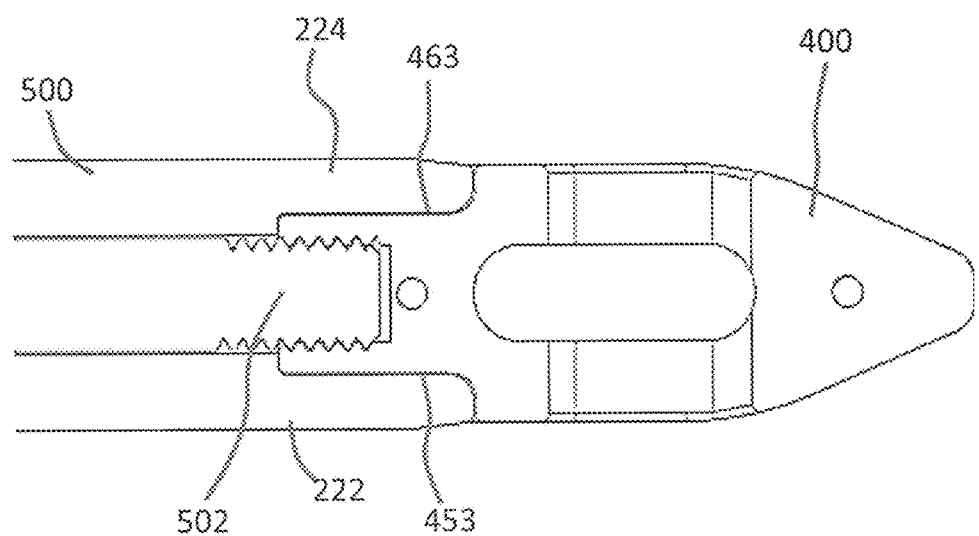
FIG. 16 is a close-up view of the inserter connected to the back end of the spacer.

Turning now to FIGS. 15 and 16, the spacer 400 may be connected to an instrument 500, similar to instrument 200 described herein. Instead of a splayed connection feature, the first and second forks 222, 224 of the gripper 220 may be fixed tabs. For example, gripper 220 may include first fork 222 configured to engage and mate with the first indentation 453 and second fork 224 configured to engage and mate with the second indentation 463. In addition, instrument 500 may include a threaded connector 502. Threaded connector 502 may have a plurality of outer threads configured to engage a threaded connection point or internally threaded opening 126 on the posterior face 122 of the implant 400. The firm connection between the instrument 500 and the spacer 400 allow the implant to be inserted on its side (e.g., view in FIG. 13) and then rotated into its final position (e.g., view in FIG. 14).

When implanting a traditional spinal interbody device in a disc space with lordosis, it is difficult to fit an implant with a height that matches the anterior height of the disk space, due to the substantially smaller posterior height of said disc space. Implant 400 is designed such that it can be initially implanted on its side and subsequently rotated 90° to its final position. This allows the spacer 400 to go into the disc space initially with its width being considered its starting height. Once in the disc space, the spacer 400 is rotatable to its final position, allowing the initially desired anterior height and lordosis.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A method of inserting an implant between adjacent vertebrae, the method comprising:
   attaching an insertion tool to the implant, wherein the implant comprises an elongate body having:
      a central longitudinal axis extending through the body;
      an anterior portion and a posterior portion, the posterior portion having a posterior wall and an internally threaded opening;
      a superior surface extending between the anterior portion and the posterior portion;
      an inferior surface extending between the anterior portion and the posterior portion;
      a first sidewall extending between the superior surface and the inferior surface on a first side of the central longitudinal axis; and
      a second sidewall extending between the superior surface and the inferior surface on a second side of the central longitudinal axis, the first sidewall and the second sidewall comprising a first indentation and a second indentation, respectively, proximate the posterior portion,
   wherein an intersection of the first sidewall and the superior surface comprises a first chamfered edge and wherein an intersection of the second sidewall and the inferior surface comprises a second chamfered edge,
   wherein the posterior wall is perpendicular to the first side wall and the second sidewall; and
   wherein the insertion tool comprises:
      a handle; and
      a gripper extending distally from the handle, the gripper having a first fork and a second fork extending generally parallel to the first fork, wherein a gap is provided between the first fork and the second fork, the gap being sized to allow the first fork to be inserted into the first indentation and the second fork into the second indention;
   inserting the implant between the adjacent vertebrae in a first orientation with the first and second sidewalls configured to contact the adjacent vertebrae; and
   rotating the implant 90° to a second orientation with the superior and inferior surfaces configured to contact the adjacent vertebrae.

2. The method of claim 1, wherein the superior surface and the inferior surface comprise a plurality of teeth.

3. The method of claim 2, wherein the plurality of teeth comprises discrete pyramidal teeth.

4. The method of claim 3, wherein one of the pyramidal teeth has a first surface formed from a tip to a base of the pyramid facing the first sidewall and a second surface formed from the tip to the base of the pyramid facing the second sidewall, the first and second surfaces being generally equidistant.

5. The method of claim 4, wherein a third surface from the tip to the base facing the anterior portion being longer than a fourth surface from the tip to the base facing the posterior portion of the implant.

6. The method of claim 1, wherein the first indentation includes a superior sidewall surface, an inferior sidewall surface, and a side surface extending between and connecting the respective superior sidewall surface and the inferior sidewall surface, the superior sidewall surface and the side surface being connected with a first curved portion and the side surface and the inferior sidewall surface being connected with a second curved portion.

7. The method of claim 6, wherein the first indentation terminates at a curved wall such that the wall connects the superior sidewall surface and the inferior sidewall surface with a semi-circular configuration.

8. The method of claim 1, wherein the anterior portion comprises a first side wall extending obliquely toward the central longitudinal axis and a second side wall extending obliquely toward the central longitudinal axis.

9. The method of claim 1, wherein the anterior portion include a nose free of teeth.

10. The method of claim 1, wherein the body has an opening extending therethrough between the superior surface and the inferior surface.

11. The method of claim 1, wherein the insertion tool further comprises a threaded connector having a plurality of outer threads configured to engage the internally threaded opening in the posterior portion of the implant.

12. A method of inserting an implant between adjacent vertebrae, the method comprising:
attaching an insertion tool to the implant, wherein the implant comprises an elongate body having:
a central longitudinal axis extending through the body;
an anterior portion and a posterior portion, the posterior portion having a posterior sidewall and an internally threaded opening;
a superior surface extending between the anterior portion and the posterior portion;
an inferior surface extending between the anterior portion and the posterior portion;
a first sidewall extending between the superior surface and the inferior surface on a first side of the central longitudinal axis; and
a second sidewall extending between the superior surface and the inferior surface on a second side of the central longitudinal axis, the first sidewall and the second sidewall comprising a first indentation and a second indentation, respectively, proximate the posterior portion, wherein the first indentation includes a superior sidewall surface, an inferior sidewall surface, and a side surface extending between and connecting the respective superior sidewall surface and the inferior sidewall surface, the superior sidewall surface and the side surface being connected with a first curved portion and the side surface and the inferior sidewall surface being connected with a second curved portion, wherein the first indentation terminates at a curved wall such that the wall connects the superior sidewall surface and the inferior sidewall surface with a semi-circular configuration,
wherein an intersection of the first sidewall and the superior surface comprises a first chamfered edge and wherein an intersection of the second sidewall and the inferior surface comprises a second chamfered edge,
wherein the posterior sidewall is perpendicular to the first sidewall and the second sidewall; and
wherein the insertion tool comprises:
a handle; and
a gripper extending distally from the handle, the gripper having a first fork having a curved portion configured to mate with the curved wall of the first indentation,
inserting the implant between the adjacent vertebrae in a first orientation with the first and second sidewalls configured to contact the adjacent vertebrae; and
rotating the implant 90° to a second orientation with the superior and inferior surfaces configured to contact the adjacent vertebrae.

13. The method of claim 12, wherein the superior surface and the inferior surface comprise a plurality of teeth.

14. The method of claim 13, wherein the plurality of teeth comprises discrete pyramidal teeth.

15. The method of claim 14, wherein one of the pyramidal teeth has a first surface formed from a tip to a base of the pyramid facing the first sidewall and a second surface formed from the tip to the base of the pyramid facing the second sidewall, the first and second surfaces being generally equidistant.

16. The method of claim 15, wherein a third surface from the tip to the base facing the anterior portion being longer than a fourth surface from the tip to the base facing the posterior portion of the implant.

17. The method of claim 12, wherein the second indentation includes a superior sidewall surface, an inferior sidewall surface, and a side surface extending between and connecting the respective superior sidewall surface and the inferior sidewall surface, the superior sidewall surface and the side surface being connected with a first curved portion and the side surface and the inferior sidewall surface being connected with a second curved portion.

18. The method of claim 17, wherein the second indentation terminates at a curved wall such that the wall connects the superior sidewall surface and the inferior sidewall surface with a semi-circular configuration.

19. The method of claim 18, wherein the gripper has a second fork having a curved portion configured to mate with the curved wall of the second indentation.

20. The method of claim 12, wherein the insertion tool further comprises a threaded connector having a plurality of outer threads configured to engage the internally threaded opening in the posterior portion of the implant.

* * * * *